(12) United States Patent
Yang et al.

(10) Patent No.: US 11,919,835 B2
(45) Date of Patent: Mar. 5, 2024

(54) METHOD FOR PREPARING PREGABALIN

(71) Applicant: ZHEJIANG HUAHAI PHARMACEUTICAL CO., LTD, Zhejiang (CN)

(72) Inventors: Changming Yang, Zheijang (CN); Pan Guo, Zheijang (CN); Yifeng Wang, Zheijang (CN); Wenling Zhang, Zheijang (CN); Peng Wang, Zheijang (CN)

(73) Assignee: ZHEJIANG HUAHAI PHARMACEUTICAL CO., LTD, Zhejiang (CN)

(*) Notice: Subject to any disclaimer, the term of this patent is extended or adjusted under 35 U.S.C. 154(b) by 729 days.

(21) Appl. No.: 17/112,917

(22) Filed: Dec. 4, 2020

(65) Prior Publication Data

US 2021/0114972 A1 Apr. 22, 2021

Related U.S. Application Data

(63) Continuation of application No. PCT/CN2018/090070, filed on Jun. 6, 2018.

(51) Int. Cl.
 *C12N 9/90* (2006.01)
 *C07C 229/08* (2006.01)
 *C12N 9/60* (2006.01)

(52) U.S. Cl.
 CPC ............. *C07C 229/08* (2013.01); *C12N 9/60* (2013.01); *C12N 9/90* (2013.01)

(58) Field of Classification Search
 CPC .......... C12Y 301/01003; C12P 41/006; C12P 13/005; C12N 9/90; C12N 9/60
 See application file for complete search history.

(56) References Cited

FOREIGN PATENT DOCUMENTS

| CN | 104557583 | 4/2015 |
|---|---|---|
| WO | WO2008127646 | 10/2008 |
| WO | WO2012059830 | 10/2012 |
| WO | WO2019/232708 | 12/2019 |

OTHER PUBLICATIONS

International Search Report regarding App. No. PCT/CN2018/090070 dated Mar. 12, 2019; 4 pages.

*Primary Examiner* — Tekchand Saidha
(74) *Attorney, Agent, or Firm* — FOLEY & LARDNER LLP

(57) ABSTRACT

The present invention relates to a method for preparing pregabalin by a biological enzyme method. In particular, the method comprises producing pregabalin B and an R-configuration compound C by using a compound A as a raw material under the action of a biological enzyme; performing configuration inversion of the separated and recovered R-configuration compound C under the action of an isomerase to produce an S-configuration compound D; and producing pregabalin B from the compound D under the action of a biological enzyme.

20 Claims, 1 Drawing Sheet

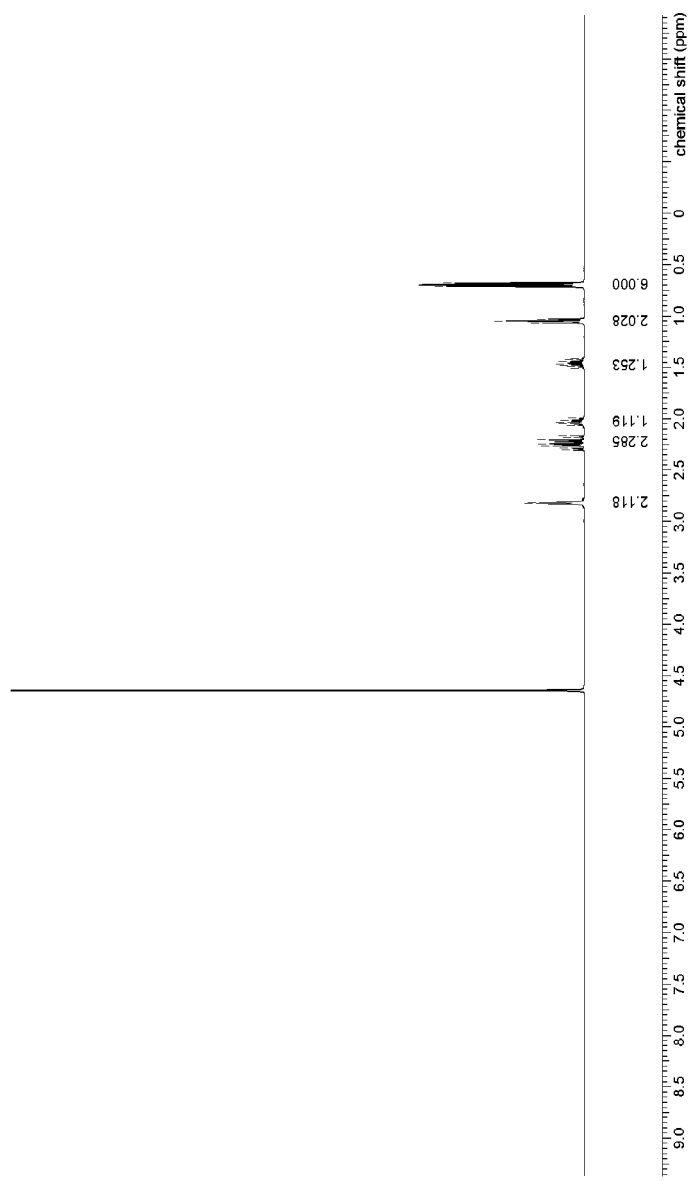

METHOD FOR PREPARING PREGABALIN

CROSS-REFERENCE TO RELATED APPLICATIONS

This application is a Continuation of PCT/CN2018/090070, filed on Jun. 6, 2018, the entire disclosure of which is incorporated herein by reference.

TECHNICAL FIELD

The present invention relates to a novel biological enzyme method for preparing pregabalin, which can be applied to the technical field of drug synthesis.

BACKGROUND

The chemical name of pregabalin is (3S)-(+)-3-aminomethyl-5-methylhexanoic acid, and its structural formula is as follows:

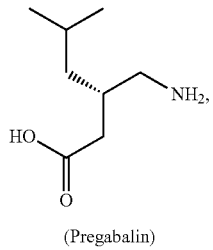

(Pregabalin)

which is an aminobutyric acid (GABA) receptor antagonist developed by Pfizer from the United States. Pregabalin is an anti-convulsant, anti-epileptic and anxiolytic drug with low dosing frequency, low dosage and few side effects. Pregabalin can be used for treating pain in central nervous system and spinal cord injury, and also treating diabetic peripheral neuralgia, postherpetic neuralgia, central neuropathic pain and fibromyalgia. Pregabalin is the drug of choice certified by the United States and Europe for the treatment of postherpetic neuralgia and diabetic peripheral neuralgia and has broad market prospects.

At present, there are extensive researches on the chemical synthesis of pregabalin in literature reports, and there are many synthetic routes, mainly including chemical resolution methods using chiral resolution reagents and asymmetric synthesis methods using asymmetric catalysts and chiral ligands.

Such methods, either steps are complicated, or the reaction conditions are harsh, and environmental pollution problems are widespread, which largely restrict the industrial applications of these methods.

In view of the good drug prospects of pregabalin, it is necessary to develop a process route with mild reaction conditions, few reaction steps, environmental friendliness, high optical purity of the obtained product pregabalin, and easy industrial production.

SUMMARY

The objectives of the present invention are to overcome the disadvantages of chemical resolution technology such as high toxicity of the resolution reagents, high price, complicated operation steps, difficult resolution, low conversion rate, low optical purity of the resolution product and difficulty in industrialization, and to provide a novel method for preparing pregabalin with high atom utilization rate, high stereoselectivity and low environmental pollution, which overcomes the limitation that the yield in the chemical resolution method can only be less than 50%, in theory, the raw materials can be 100% converted into the final product. In order to achieve the above objectives, the present invention adopts the following technical solutions:

A method for preparing pregabalin, comprising the following steps:

step 1:

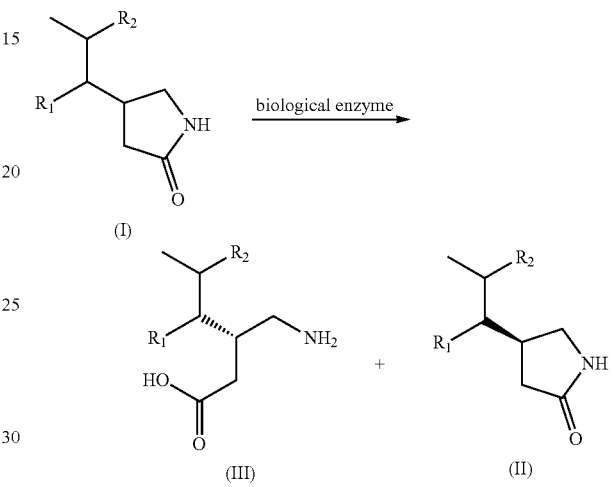

under the action of a biological enzyme, producing target compound (III) and by-product (II) from compound (I) in a solvent;

step 2:

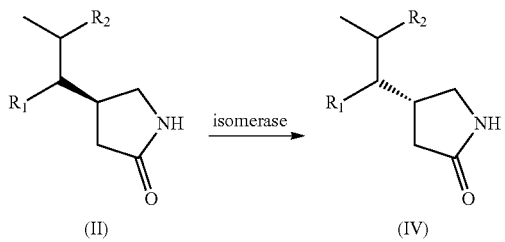

under the action of an isomerase, performing configuration inversion of the compound (II) obtained in step 1 in a solvent to produce compound (IV);

step 3:

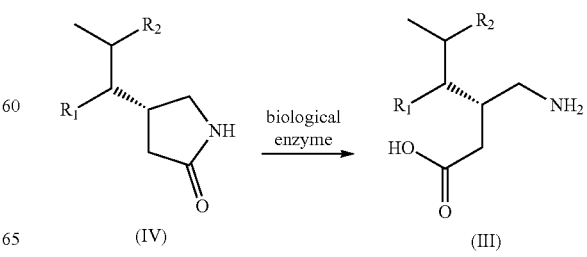

under the action of the biological enzyme in step 1, producing target compound (III) from the compound (IV) obtained in step 2 in a solvent;

wherein $R^1$ and $R^2$ are independently hydrogen atom or an alkyl group, and the alkyl group is preferably $C_1$-$C_4$ branched or straight chain alkyl group; the alkyl group can specifically be methyl, ethyl, propyl, isopropyl, n-butyl, tert-butyl or isobutyl.

When $R^1$ is H and $R^2$ is methyl, the corresponding compound III is pregabalin.

The specific reaction process is as follows:

step 1:

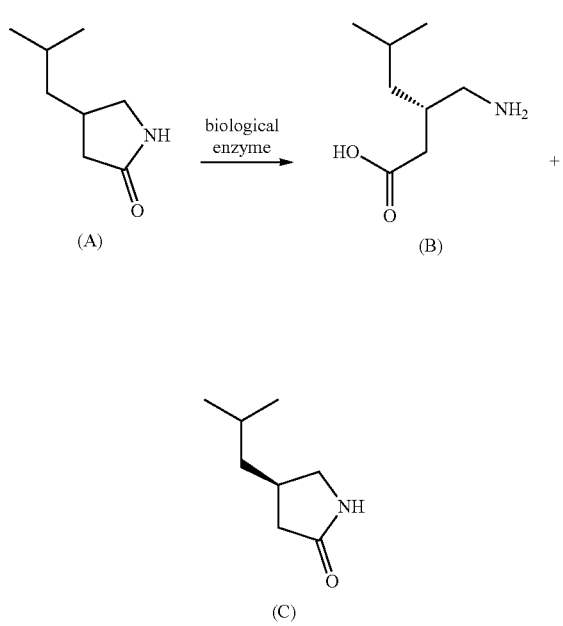

under the selective action of a biological enzyme, hydrolyzing the S-configuration compound, in racemic compound (A) as the substrate for enzymatic hydrolysis, into target compound (B) (pregabalin); R-configuration compound (C) is retained without being hydrolyzed;

step 2:

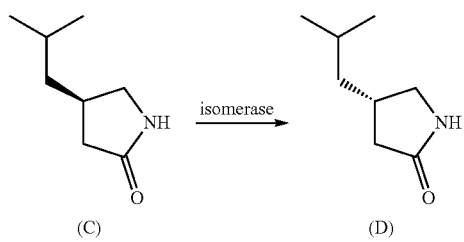

under the action of an isomerase, performing configuration inversion of the R-configuration compound (C) separated and recovered from step 1 to produce S-configuration compound (D);

step 3:

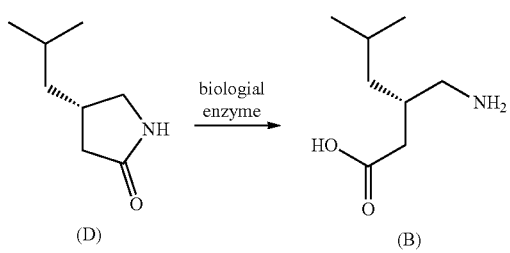

hydrolyzing the S-configuration compound (D) obtained in step 2 directionally into target compound (B) (pregabalin) by the biological enzyme in step 1.

In the method of the present application, in steps 1 and 3, the biological enzyme is a hydrolase, specifically a specific type of lipase, preferably a mold lipase, such as Lipase from *Rhizopus delemar*, Lipase from *Aspergillus niger*, Lipase from *Rhizomucor miehei*, Lipase from *Gertrichum candidum*; a yeast lipase, such as Lipase from *Candida* (including Lipase from *Candida antarctica* B and Lipase from *Candida cylindracea*), Lipase from *Rhodoaorula glutinis*; a bacterial lipase, such as Lipase from *Burkholderia cepacia*, Lipase from *Pseudomonas*, Lipase from *Staphylococcus epidermidis*. Among the lipases, more preferred are mold lipases such as Lipase from *Rhizopus delemar* and Lipase from *Gertrichum candidum*, yeast lipases such as Lipase from *Candida antarctica* B and Lipase from *Candida cylindracea*, and bacterial lipases such as Lipase from *Burkholderia cepacia*.

In steps 1 and 3, the form of the biological enzyme can be immobilized enzyme particles or enzyme powder after freeze-drying, or enzyme-containing cells or organelles after extraction, concentration and dehydration processes. The enzymes used can be commercial enzymes or crude enzymes obtained by culturing enzyme-producing microorganisms.

In step 2, the isomerase is specifically a specific type of epimerase (i.e., a mutarotase), preferably glucose isomerase, sucrose isomerase, D-tagatose 3-epimerase, D-psicose 3-epimerase, cellobiose 2-epimerase, 2-ketogluconate epimerase. Among the epimerases, glucose isomerase, sucrose isomerase and cellobiose 2-epimerase are more preferred.

In step 2, the form of the isomerase can be immobilized enzyme particles or enzyme powder after freeze-drying, or enzyme-containing cells or organelles after extraction, concentration and dehydration processes. The enzymes used can be commercial enzymes or crude enzymes obtained by culturing enzyme-producing microorganisms.

In step 1, the mass ratio of the biological enzyme to the compound (I) or (A) is 1:2-1:20, preferably 1:5-1:10.

In step 2, the mass ratio of the isomerase to the compound (II) or (C) obtained in step 1 is 1:1-1:20, preferably 1:3-1:9.

In step 3, the mass ratio of the biological enzyme to the compound (IV) or (D) obtained in step 2 is 1:2-1:20, preferably 1:5-1:10.

In steps 1 and 3, the solvent is water or a miscible system of water and organic solvent, preferably a miscible system of water and organic solvent. Preferably, the organic solvent is alcohols, ethers or ketones, more preferably one or more of isopropanol, n-butanol, tert-butanol, tetrahydrofuran, 1,4-dioxane, acetone and cyclohexanone ("more" in the present application refers to two or more than two), further preferably acetone and isopropanol; preferably, as to the mixing ratio of water to organic solvent in the miscible system of water and organic solvent, the volume ratio of water to organic solvent is 2:1-50:1, more preferably 10:1. The mass-volume ratio of compound I (or (A)) or IV (or (D)) to the solvent is 1 g:10 mL-1 g:50 mL, preferably 1 g:10 mL-1 g:20 mL.

In steps 1 and 3, the pH value of the solvent for the enzymatic hydrolysis reaction is 7.0-10.0, preferably 9.0-10.0. The aqueous solutions of alkali metal carbonate, alkali metal bicarbonate and alkali metal hydroxide or different kinds of buffer solutions are used to control the pH. The alkali metal carbonate is preferably sodium carbonate and potassium carbonate, the alkali metal bicarbonate is preferably sodium bicarbonate and potassium bicarbonate, the alkali metal hydroxide is preferably sodium hydroxide and potassium hydroxide; the buffer solution is preferably Gly-NaOH buffer solution (100 mmol/L, pH 9.0-10.0).

In step 2, the solvent used is an organic solvent, preferably alcohols or ketones, more preferably isopropanol, n-butanol, tert-butanol, acetone and the like. The mass-volume ratio of compound II or (C) to the solvent is 1 g:10 mL-1 g:50 mL, preferably 1 g:10 mL-1 g:20 mL.

In steps 1, 2 and 3, the reaction time is 5-20 h, preferably 5-10 h.

In steps 1, 2 and 3, the reaction temperature is 25-55° C., preferably 35-45° C.

Between the step 1 and step 2, a step of extracting the product solution of step 1 is also included, and the organic solvent used for extraction is selected from toluene, dichloromethane, methyl tert-butyl ether or ethyl acetate etc., preferably ethyl acetate.

In the steps 1, 2 and 3, the optical purity of the product is detected by chiral high performance liquid chromatography. The chromatographic conditions are as follows: the chromatograph used is Agilent HPLC 1260; the detector used is a UV variable wavelength detector with a detection wavelength of 210 nm; the chromatographic column used is Inertsil ODS-3 (250×4.6 mm, 5 μm), and the column temperature is 30° C.; the mobile phase is buffer solution:acetonitrile:methanol=84:5:11 (V/V/V), where the buffer solution is 0.04M aqueous solution of diammonium hydrogen phosphate, adjusted to pH 6.6 with phosphoric acid; Flow rate: 0.8 mL/min; Injection volume: 50 μL.

The present invention provides a method for preparing pregabalin with a biological enzyme as the catalyst, which has the advantages of fewer steps, simple operation, mild conditions, environmental protection, low cost, high atom utilization, high product optical purity and so on. Compared with traditional chemical resolution method, the method of the present invention can synthesize pregabalin in a greener, simpler, and more efficient manner, and has high industrial application value.

DESCRIPTION OF THE DRAWINGS

FIG. 1 is the hydrogen nuclear magnetic resonance spectrum of compound (B) prepared in Example 1.

DETAILED DESCRIPTION

In order to better understand the content of the present invention, the technical solutions of the present invention will be described with specific examples below, but the protection scope of present invention is not limited to the examples.

In the described examples, the compound (A) (4-isobutyl-2-pyrrolidone) used in step 1 is a commercially available chemical; the biological enzymes used in steps 1 and 3, and the isomerase used in step 2 are commercially available enzymes.

The embodiments of the present invention will be described in further detail below in conjunction with the examples. The following examples are only used to illustrate the present invention, but not to limit the scope of the present invention.

EXAMPLE 1

Step 1: 50 g of compound (A) (producer: Nanjing Bomier Biotechnology Co., Ltd., purity 98%), 450 mL of water, and 50 mL of acetone were added into a reaction flask, stirred and the temperature was raised to 35° C., the pH value of the system was adjusted to 9-10 with sodium carbonate solution (with a mass fraction of 10%), 10 g of Lipase from *Candida antarctica* B (producer: Hangzhou Novocata Biotechnology co., Ltd., purity 98%) was added, the temperature was kept and the reaction solution was stirred for 5 h. After reacting for 1 h, a pH test paper was used to detect the pH change of the reaction solution every 1 h, and an appropriate amount of sodium carbonate solution was added to maintain the pH range of 9-10. After the reaction was completed, the biological enzyme was removed by filtration. The reaction solution was extracted twice with 150 mL of ethyl acetate. The organic layer was washed with water to neutrality, concentrated under reduced pressure to about ⅓ volume, cooled to 5-10° C., filtered and dried to obtain 21.6 g of by-product R-configuration compound (C) with a yield of 43.2%, and the product enantiomeric excess value ee: 98.21%; the pH value of the water layer was adjusted to 6.5-7.5 with hydrochloric acid, cooled to 5-10° C., filtered and dried to obtain 25.5 g of the target product compound (B) pregabalin with a yield of 45.2%, and the product enantiomeric excess value e.e.: 99.74%. The hydrogen nuclear magnetic resonance spectrum of the product is shown in FIG. 1, and the specific data are as follows: $^1$H-NMR($D_2O$): δ 0.7(t, J=8.0 Hz, 6H, $CH_3$), 1.05(t, J=8.0 Hz, 2H, $CH_2$), 1.44-1.46(m, 1H, CH), 2.03-2.05(m, 1H, CH), 2.17-2.29(m, 2H, $CH_2COOH$), 2.82(d, J=8.0 Hz, 2H, $CH_2NH_2$), the above data confirms that the chemical structure is pregabalin.

Step 2: 20 g of R-configuration compound (C) obtained in step 1, 200 mL of isopropanol were added into a reaction flask, stirred and the temperature was raised to 35° C., 5 g of glucose isomerase (producer: Jinjinle Chemical Co., Ltd., purity 98%) was added, the temperature was kept and the reaction solution was stirred for 10 h, after the reaction was completed, the isomerase was removed by filtration, the filtrate was concentrated to about ⅓ volume, 50 mL water was added, cooled to 0-5° C., filtered and dried to obtain 17.7 g of S-configuration compound (D) with a yield of 88.5%, the product enantiomeric excess value, i.e., ee value was 98.76%.

Step 3: 15 g of the S-configuration compound (D) obtained in step 2, 200 mL of water, and 100 mL of isopropanol were added into a reaction flask, stirred and the temperature was raised to 35° C., the pH value of the system was adjusted to 10 with sodium carbonate solution (with a mass fraction of 10%), 3 g of Lipase from *Candida antarctica* B (producer: Shanghai Yuanye Bio-Technology Co., Ltd., purity 98%) was added. The temperature was kept and the reaction solution was stirred for 5 h, after reacting for 1 h, an appropriate amount of sodium carbonate solution was added every 1 h to maintain the pH value in the range of 9-10. After the reaction was completed, the biological enzyme was removed by filtration, the filtrate was concentrated to ⅔ volume under reduced pressure, the pH value was adjusted to 6.5-7.5 with hydrochloric acid, cooled to 5-10° C., filtered and dried to obtain 15.4 g of target compound (B) pregabalin with a yield of 91.3%, product enantiomeric excess value e.e.: 99.22%, the hydrogen nuclear magnetic resonance spectrum of the product is shown in FIG. 1, and the specific data are as follows: $^1$H-NMR(D$_2$O): δ 0.7(t, J=8.0 Hz, 6H, CH$_3$), 1.05(t, J=8.0 Hz, 2H, CH$_2$), 1.44-1.46(m, 1H, CH), 2.03-2.05(m, 1H, CH), 2.17-2.29(m, 2H, CH$_2$COOH), 2.82(d, J=8.0 Hz, 2H, CH$_2$NH$_2$), the above data confirms that the chemical structure is pregabalin.

EXAMPLE 2

Step 1: 50 g of compound (A) (producer: Nanjing Bomier Biotechnology Co., Ltd., purity 98%), 350 mL of water, 50 mL of tetrahydrofuran, 100 mL of Gly-NaOH buffer solution (100 mmol/L, pH 9.0-10.0) were added into a reaction flask, stirred and the temperature was raised to 35° C., 10 g of Lipase from *Rhizopus delemar* (producer: Guangzhou LES Biological Technology Co., Ltd., purity 98%) was added, the temperature was kept and the reaction solution was stirred for 9 h. After the reaction was completed, the biological enzyme was removed by filtration, the reaction solution was extracted twice with a total of 150 mL of methyl tert-butyl ether. The organic layer was washed with water to neutrality, the solvent was concentrated to about ⅓ volume, cooled to 5-10° C., filtered and dried to obtain 23.1 g of by-product R-configuration compound (C) with a yield of 46.2%, and the product enantiomeric excess value ee: 98.72%; the pH value of the water layer was adjusted to 6.5-7.5 with hydrochloric acid, cooled to 5-10° C., filtered and dried to obtain 25.9 g of the target product compound (B) pregabalin with a yield of 45.9%, the product enantiomeric excess value e.e.: 99.71%, and the hydrogen nuclear magnetic resonance spectrum of the product was the same as FIG. 1.

Step 2: 15 g of R-configuration compound (C) obtained in step 1, 150 mL of acetone were added into a reaction flask, stirred and the temperature was raised to 35° C., 5 g of sucrose isomerase (producer: Nantong Feiyu Biological Technology Co., Ltd., purity 98%) was added, the temperature was kept and the reaction solution was stirred for 10 h, after the reaction was completed, the isomerase was removed by filtration, the filtrate was concentrated to about ⅓ volume, cooled to −10-0° C., suction filtered and dried to obtain 13.8 g of S-configuration compound (D) with a yield of 92.0%, the product enantiomeric excess value e.e.: 99.02%.

Step 3: 10 g of the compound (D) obtained in step 2 and 300 mL of water were added into a reaction flask, stirred and the temperature was raised to 35° C., the pH value of the system was adjusted to 10 with sodium carbonate solution (with a mass fraction of 10%), 2 g of Lipase from *Rhizopus delemar* (producer: Guangzhou LES Biological Technology Co., Ltd., purity 98%) was added. The temperature was kept and the reaction solution was stirred for 5 h, after reacting for 1 h, sodium carbonate solution was added every 1 h to maintain the pH value in the range of 9-10. After the reaction was completed, the biological enzyme was removed by filtration, the pH value of the filtrate was adjusted to 6.5-7.5 with hydrochloric acid, cooled to 5-10° C., filtered and dried to obtain 10.5 g of target compound (B) pregabalin with a yield of 93.2%, the product enantiomeric excess value e.e.: 99.22%, and the hydrogen nuclear magnetic resonance spectrum of the product was the same as FIG. 1.

EXAMPLE 3

Step 1: 50 g of compound (A) (producer: Nanjing Bomier Biotechnology Co., Ltd., purity 98%) and 750 mL of water were added into a reaction flask, stirred and the temperature was raised to 35° C., the pH value of the system was adjusted to 9 with sodium hydroxide solution (with a mass fraction of 5%), 5 g of Lipase from *Burkholderia cepacia* (producer: Meryer (Shanghai) Chemical Technology Co., Ltd., purity 98%) was added, the temperature was kept and the reaction solution was stirred for 6 h. After reacting for 1 h, a pH test paper was used to monitor the pH change of the reaction solution every 1 h, and sodium hydroxide solution (with a mass fraction of 5%) was added to maintain the pH range of 9-10. After the reaction was completed, the biological enzyme was removed by filtration, extracted twice with a total of 250 mL of toluene. The organic layer was concentrated to ⅓ volume, cooled to 5-10° C., filtered and dried to obtain 23.5 g of by-product R-configuration compound (C) with a yield of 47.0%, and the product enantiomeric excess value e.e.: 97.98%; the pH value of the water layer was adjusted to 6.5-7.5 with hydrochloric acid, cooled to 5-10° C., filtered and dried to obtain 26.7 g of the target product compound (B) pregabalin with a yield of 47.3%, and the product enantiomeric excess value e.e.: 99.83%, the hydrogen nuclear magnetic resonance spectrum of the product is the same as FIG. 1.

Step 2: 15 g of R-configuration compound (C) obtained in step 1, 150 mL of n-butanol were added into a reaction flask, stirred and the temperature was raised to 35° C., 6 g of cellobiose 2-epimerase (producer: Shanghai Baoman Biological Technology Co., Ltd., purity 98%) was added, the temperature was kept and the reaction solution was stirred for 10 h, after the reaction was completed, the isomerase was removed by filtration, the filtrate was concentrated to about ⅓ volume, 50 mL of water was added, cooled to 0-5° C., suction filtered and dried to obtain 14.1 g of S-configuration compound (D) with a yield of 94.0%, the product enantiomeric excess value e.e.: 99.72%.

Step 3: 10 g of compound (D) obtained in step 2, 200 mL of water, and 20 mL of cyclohexanone were added into a reaction flask, stirred and the temperature was raised to 35° C., the pH value of the system was adjusted to 10 with saturated sodium carbonate solution, 4 g of Lipase from *Burkholderia cepacia* (producer: Meryer (Shanghai) Chemical Technology Co., Ltd., purity 98%) was added, the temperature was kept and the reaction solution was stirred for 7 h, after reacting for 1 h, sodium carbonate solution was added every 1 h to maintain the pH value in the range of 8-10. After the reaction was completed, the biological enzyme was removed by filtration, the pH value of the filtrate was adjusted to 6.5-7.5 with hydrochloric acid, cooled to 5-10° C., filtered and dried to obtain 10.2 g of target compound (B) pregabalin with a yield of 90.3%, product enantiomeric excess value e.e.: 99.64%, the hydrogen nuclear magnetic resonance spectrum of the product is the same as FIG. 1.

EXAMPLE 4

Step 1: 50 g of compound (A) (producer: Nanjing Bomier Biotechnology Co., Ltd., purity 98%), 450 mL of water and 50 mL of 1,4-dioxane were added into a reaction flask, stirred and the temperature was raised to 45° C., the pH value of the system was adjusted to 10 with potassium hydroxide solution (with a mass fraction of 5%), 5 g of Lipase from *Gertrichum candidum* (producer: Shanghai Macklin Biochemical Co., Ltd., purity 97%) was added, the temperature was kept and the reaction solution was stirred for 5 h. After reacting for 1 h, a pH test paper was used to monitor the pH change of the reaction solution every 1 h, and an appropriate amount of potassium hydroxide solution was added to maintain the pH range of 9-10. After the reaction was completed, the biological enzyme was removed by filtration. The reaction solution was extracted twice with a total of 250 mL of toluene. The organic layer was washed with water to neutrality, the filtrate was concentrated to ⅓ volume, cooled to 5-10° C., filtered and dried to obtain 23.3 g of by-product R-configuration compound (C) with a yield of 46.6%, and the product enantiomeric excess value ee: 97.08%; the pH value of the water layer was adjusted to 6.5-7.5 with hydrochloric acid, cooled to 5-10° C., filtered and dried to obtain 25.8 g of the target product compound (B) pregabalin with a yield of 45.8%, and the product enantiomeric excess value e.e.: 99.91%, the hydrogen nuclear magnetic resonance spectrum of the product is the same as FIG. 1.

Step 2: 15 g of R-configuration compound (C) obtained in step 1, 150 mL of tert-butanol were added into a reaction flask, stirred and the temperature was raised to 45° C., 6 g of D-tagatose 3-epimerase (producer: Shanghai Baoman Biological Technology Co., Ltd., purity 97%) was added, the temperature was kept and the reaction solution was stirred for 10 h, after the reaction was completed, the isomerase was removed by filtration, the filtrate was concentrated to about ¼ volume, 200 mL of water was added, cooled to 5-10° C., suction filtered and dried to obtain 14.1 g of S-configuration compound (D) with a yield of 94.0%, the product enantiomeric excess value e.e.: 99.72%.

Step 3: 10 g of compound (D) obtained in step 2, 200 mL of water, and 100 mL of tert-butanol were added into a reaction flask, stirred and the temperature was raised to 40° C., the pH value of the system was adjusted to 10 with saturated sodium bicarbonate solution, 5 g of Lipase from *Gertrichum candidum* (producer: Shanghai Macklin Biochemical Co., Ltd., purity 97%) was added, the temperature was kept and the reaction solution was stirred for 5 h, after reacting for 1 h, sodium bicarbonate solution was added every 1 h to maintain the pH value in the range of 9-10. After the reaction was completed, the biological enzyme was removed by filtration, the filtrate was concentrated under reduced pressure to ⅔ volume, the pH value was adjusted to 6.5-7.5 with hydrochloric acid, cooled to 5-10° C., filtered and dried to obtain 10.2 g of target compound (B) pregabalin with a yield of 90.3%, product enantiomeric excess value e.e.: 99.64%, the hydrogen nuclear magnetic resonance spectrum of the product is the same as FIG. 1.

EXAMPLE 5

Step 1: 50 g of compound (A) (producer: Nanjing Bomier Biotechnology Co., Ltd., purity 98%), 450 mL of water and 50 mL of n-butanol were added into a reaction flask, stirred and the temperature was raised to 35° C., the pH value of the system was adjusted to 9-10 with sodium carbonate solution (with a mass fraction of 10%), 10 g of Lipase from *Candida cylindracea* (producer: Hangzhou Novocata Biotechnology co., Ltd., purity 98%) was added, the temperature was kept and the reaction solution was stirred for 5 h. After reacting for 1 h, a pH test paper was used to detect the pH change of the reaction solution every 1 h, and an appropriate amount of sodium carbonate solution was added to maintain the pH range of 9-10. After the reaction was completed, the biological enzyme was removed by filtration. The reaction solution was extracted twice with 150 mL of ethyl acetate. The organic layer was washed with water to neutrality, concentrated under reduced pressure to about ⅓ volume, cooled to 5-10° C., filtered and dried to obtain 19.8 g of by-product R-configuration compound (C) with a yield of 39.6%, and the product enantiomeric excess value ee: 98.91%; the pH value of the water layer was adjusted to 6.5-7.5 with hydrochloric acid, cooled to 5-10° C., filtered and dried to obtain 25.5 g of the target product compound (B) pregabalin with a yield of 45.2%, and the product enantiomeric excess value e.e.: 99.12%, the hydrogen nuclear magnetic resonance spectrum of the product is the same as FIG. 1.

Step 2: 15 g of R-configuration compound (C) obtained in step 1, 150 mL of n-butanol were added into a reaction flask, stirred and the temperature was raised to 35° C., 6 g of cellobiose 2-epimerase (producer: Shanghai Baoman Biological Technology Co., Ltd., purity 97%) was added, the temperature was kept and the reaction solution was stirred for 15 h, after the reaction was completed, the isomerase was removed by filtration, the filtrate was concentrated to about ⅓ volume, 50 mL of water was added, cooled to 0-5° C., suction filtered and dried to obtain 13.8 g of S-configuration compound (D) with a yield of 92.0%, the product enantiomeric excess value e.e.: 99.65%.

Step 3: 10 g of compound (D) obtained in step 2 and 300 mL of water were added into a reaction flask, stirred and the temperature was raised to 35° C., the pH value of the system was adjusted to 10 with sodium carbonate solution (with a mass fraction of 10%), 2 g of Lipase from *Candida cylindracea* (producer: Hangzhou Novocata Biotechnology co., Ltd., purity 98%) was added, the temperature was kept and the reaction solution was stirred for 7 h, after reacting for 1 h, sodium carbonate solution was added every 1 h to maintain the pH value in the range of 9-10. After the reaction was completed, the biological enzyme was removed by filtration, the pH value of the filtrate was adjusted to 6.5-7.5 with hydrochloric acid, cooled to 5-10° C., filtered and dried to obtain 10.2 g of target compound (B) pregabalin with a yield of 90.5%, product enantiomeric excess value e.e.: 99.31%, the hydrogen nuclear magnetic resonance spectrum of the product is the same as FIG. 1.

In steps 1, 2 and 3 described in the above examples, the biological enzymes and isomerases obtained by filtration after the reaction is completed can be recovered and reused.

The invention claimed is:

1. A method for preparing pregabalin comprising:
   reacting a compound of formula (I) in a first solvent with a biological enzyme to produce a target compound of formula (III) and a by-product of formula (II);
   reacting the by-product of formula (II) in a second solvent with an isomerase to perform a configuration inversion to produce a compound of formula (IV);
   reacting the compound of formula (IV) in a third solvent with the biological enzyme to produce the target compound of formula (III);

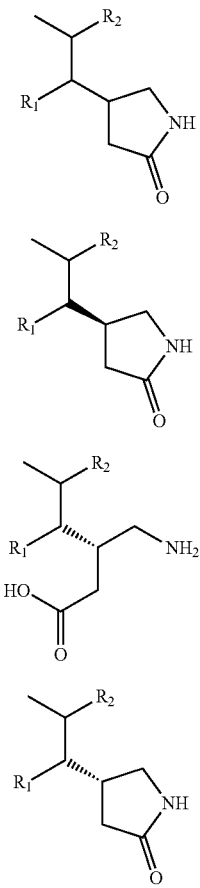

wherein:
R¹ and R² are independently hydrogen or an alkyl group; and
the biological enzyme is a hydrolase.

2. The method of claim 1, wherein the hydrolase is a lipase.

3. The method of claim 2, wherein the lipase is a mold lipase, a yeast lipase, or a bacterial lipase.

4. The method of claim 3, wherein the mold lipase is from a *Rhizopus delemar*, an *Aspergillus niger*, a *Rhizomucor miehei*, or a *Gertrichum candidum*.

5. The method of claim 3, wherein the yeast lipase is from *Candida antarctica* B, *Candida cylindracea*, or *Rhodoaorula glutinis*.

6. The method of claim 3, wherein the bacterial lipase is from *Burkholderia cepacia, Pseudomonas*, or *Staphylococcus epidermidis*.

7. The method of claim 1, wherein the isomerase is an epimerase.

8. The method of claim 7, wherein the epimerase is selected from the group consisting of glucose isomerase, sucrose isomerase, D-tagatose 3-epimerase, D-psicose 3-epimerase, cellobiose 2-epimerase and 2-ketogluconate epimerase.

9. The method of claim 1, wherein the biological enzyme, the isomerase, or both are in the form of immobilized enzyme particles, enzyme powder, or cells or organelles containing the biological enzyme or the isomerase.

10. The method of claim 1, wherein R¹ and R² are independently a $C_1$-$C_4$ branched or straight chain alkyl group.

11. The method of claim 1, wherein R¹ is H and R² is methyl.

12. The method of claim 1, wherein
the biological enzyme and the compound of formula (I) have a mass ratio of 1:2-1:20; and/or
the isomerase and the compound of formula (II) have a mass ratio of 1:1-1:20; and/or
the biological enzyme and the compound of formula (IV) have a mass ratio of 1:2-1:20.

13. The method of claim 1, wherein the first solvent and the third solvent is water or a miscible system of water and an organic solvent.

14. The method of claim 1, wherein the mass-volume ratio of the compound of formula (I) to the first solvent or the compound of formula (IV) to the third solvent is 1 g:10 mL-1 g:50 mL.

15. The method of claim 1, wherein the second solvent is an organic solvent.

16. The method of claim 1, wherein the mass-volume ratio of the compound of formula (II) to the second solvent is 1 g:10 mL-1 g:50 mL.

17. The method of claim 1, wherein the reacting a compound of formula (I), the reacting the by-product of formula (II), and/or the reacting the compound of formula (IV) is at a temperature range from 25° C. to 55° C.

18. The method of claim 1, wherein the reacting a compound of formula (I), the reacting the by-product of formula (II), and/or the reacting the compound of formula (IV) is for a time from 5 h to 20 h.

19. The method of claim 1 further comprising extracting the by-product of formula (II) before the reacting with the isomerase.

20. The method of claim 19, wherein the extracting is with a fourth organic solvent selected from the group consisting of toluene, dichloromethane, methyl tert-butyl ether, and ethyl acetate.

* * * * *